(12) United States Patent
Salvador Maturana

(10) Patent No.: US 11,395,860 B2
(45) Date of Patent: Jul. 26, 2022

(54) METHOD OF PREPARING CONTAINERS FOR BLOOD-DERIVED PRODUCTS

(71) Applicant: Grifols Worldwide Operations Limited, Dublin (IE)

(72) Inventor: Josep Salvador Maturana, Parets del Valles (ES)

(73) Assignee: GRIFOLS WORLDWIDE OPERATIONS LIMITED, Dublin (IE)

(*) Notice: Subject to any disclaimer, the term of this patent is extended or adjusted under 35 U.S.C. 154(b) by 338 days.

(21) Appl. No.: 16/808,258

(22) Filed: Mar. 3, 2020

(65) Prior Publication Data

US 2020/0282095 A1    Sep. 10, 2020

(30) Foreign Application Priority Data

Mar. 5, 2019    (EP) .................................... 19382168

(51) Int. Cl.
*A61L 2/26* (2006.01)
*A61J 1/14* (2006.01)
*A61L 2/00* (2006.01)
*A61L 2/07* (2006.01)
*A61L 2/18* (2006.01)

(52) U.S. Cl.
CPC . *A61L 2/26* (2013.01); *A61J 1/14* (2013.01); *A61L 2/0023* (2013.01); *A61L 2/07* (2013.01); *A61L 2/18* (2013.01); *A61L 2202/182* (2013.01); *A61L 2202/22* (2013.01); *A61L 2202/23* (2013.01)

(58) Field of Classification Search
CPC ..... A61L 2/07; A61L 2/18; A61L 2/26; A61L 2/0023; A61L 2202/182; A61L 2202/23; A61L 2202/22; A61J 1/14
See application file for complete search history.

(56) References Cited

U.S. PATENT DOCUMENTS

| | | |
|---|---|---|
| 4,166,096 A | 8/1979 | Gillis |
| 4,407,874 A | 10/1983 | Gehrke |
| 4,657,540 A | 4/1987 | Iwamoto |
| 4,944,919 A | 7/1990 | Powell |
| 5,653,090 A | 8/1997 | Weiss |

(Continued)

FOREIGN PATENT DOCUMENTS

| | | |
|---|---|---|
| BE | 893480 A | 10/1982 |
| CL | 201901883 | 8/2019 |

(Continued)

OTHER PUBLICATIONS

Office Action dated May 4, 2021 in Chilean Patent Application No. 2020-00429.

(Continued)

*Primary Examiner* — Sean E Conley
(74) *Attorney, Agent, or Firm* — Knobbe, Martens, Olson & Bear LLP

(57) ABSTRACT

A method of preparing containers for blood-derived products includes filling the blood-derived product containers with the blood-derived product, of virally inactivating the blood-derived product containers, and detecting possible defects in the blood-derived product containers. The viral inactivation is carried out by placing the blood-derived product containers in contact with steam at sub-atmospheric pressure in a chamber adapted for that purpose.

13 Claims, 1 Drawing Sheet

(56) References Cited

U.S. PATENT DOCUMENTS

| | | |
|---|---|---|
| 5,947,287 A | 9/1999 | Weiss |
| 7,079,759 B2 | 7/2006 | Tokutake |
| 8,865,064 B2 | 10/2014 | Meier |
| 2003/0177739 A1 | 9/2003 | Lewis |
| 2006/0088450 A1 | 4/2006 | Stecklein |
| 2007/0212282 A1 | 9/2007 | Matsui |
| 2009/0123341 A1 | 5/2009 | Eros |
| 2017/0197024 A1 | 7/2017 | Kiminami |

FOREIGN PATENT DOCUMENTS

| | | |
|---|---|---|
| CN | 108902630 A | 11/2018 |
| DE | 1933542 A1 | 6/1971 |
| DE | 202011102490 U1 | 6/2012 |
| EP | 1245217 A2 | 10/2002 |
| JP | 2007-195956 A | 8/2007 |
| KR | 101857215 B1 | 5/2018 |
| WO | WO 1995/14494 A1 | 6/1995 |
| WO | WO 2002/04860 A1 | 1/2002 |
| WO | WO 2003/043665 A1 | 5/2003 |
| WO | WO 2008/061137 A2 | 5/2008 |
| WO | WO 2016/051962 A1 | 4/2016 |
| WO | WO 2017/064819 A1 | 4/2017 |

OTHER PUBLICATIONS

Search Report dated May 4, 2021 in Chilean Patent Application No. 2020-00429.
European Search Report in corresponding European Patent Application No. 19382168.3 dated Aug. 8, 2019, 5 pages.

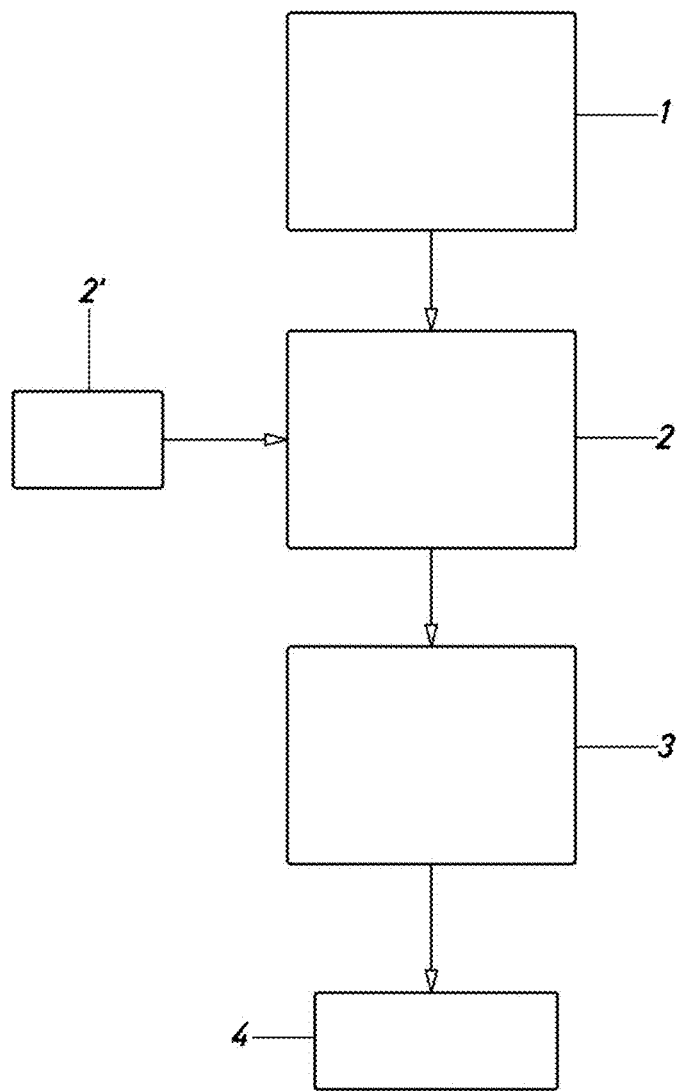

METHOD OF PREPARING CONTAINERS FOR BLOOD-DERIVED PRODUCTS

BACKGROUND

This patent application discloses a method of preparing containers for blood-derived products which has novel characteristics which are advantageous compared to known characteristics.

SUMMARY

One of the viral inactivation methods known in the prior art for this technological sector relating to blood-derived products consists in heat treatment by submerging the containers or bags of product in water. The water is heated until the product reaches a target temperature which depends on the requirements of the blood-derived product, and from that time a viral inactivation cycle using a water bath begins. During this cycle which lasts many hours, the temperature must be maintained within a very limited range. Once said cycle has ended, the product is rapidly cooled again to prevent the product from being over-exposed to high temperatures.

In the sector concerned with the preparation of blood-derived product containers, a quality control test is carried out thereon to detect possible defects in the container. However, visual inspection of the containers is not sufficient as it is difficult to detect defects, which means that many containers arrive at the end user in poor condition. On many occasions, said containers, which may be bags made of a plastics material, have defective sealing which cannot be detected with the naked eye, owing to defects such as defective welding on the container, breaks in the container, splits and porosities in the walls of the container, as well as other types of defect that cannot be seen with the naked eye. Said defects are sometimes manifested when the containers have already been made available to the customer. The present invention aims to overcome this drawback. This is achieved by subjecting the containers to a stress test during the viral inactivation phase of the product in order to amplify any defect therein so as to facilitate the detection of defects in the quality control phase by a visual inspection of the product. Said stress test has the additional advantage of replacing the viral inactivation method previously used in the sector relating to blood-derived products.

The object of the present invention is to achieve a more effective and simpler quality control whilst also replacing the conventional viral inactivation methods for blood-derived product containers.

The present invention discloses a method of carrying out a stress test simultaneously with the viral inactivation of the blood-derived product containers, which aims to overcome some of the drawbacks found in the prior art.

More particularly, the present invention discloses a method of preparing containers for blood-derived products which comprises at least:
- a filling phase of the blood-derived product containers with the blood-derived material,
- a viral inactivation phase of the blood-derived product containers,
- a quality control phase for detecting possible defects in the blood-derived product containers, in which the viral inactivation phase is carried out by placing the blood-derived product containers in contact with steam at a sub-atmospheric pressure in a chamber adapted for that purpose.

Preferably, said method comprises an additional cooling phase after the viral inactivation phase of the blood-derived product containers. More preferably, the cooling phase is carried out by recirculating cold air.

More preferably, in the viral inactivation phase the steam is 'clean', in other words, said steam has no contaminant particles. Still more preferably, the steam used in the viral inactivation phase is sanitary quality steam. The contaminant particles found in the steam may be rust, scale, dirt and sediments which may be carried by the water used to produce the steam. Sanitary quality steam is understood as steam produced from sanitary quality water, the parameters and parametric values of which meet those established by the World Health Organization in its Guidelines for drinking-water quality.

More preferably, the steam used in the viral inactivation phase is saturated steam. Alternatively, superheated steam may be used.

Preferably, the quality control phase comprises a visual inspection of the blood-derived product containers in order to locate defects in said containers. More preferably, the object of said visual inspection is to locate any containers that have defective sealing.

More preferably, the blood-derived product is albumin and the viral inactivation phase is carried out at a temperature of between 55° C. and 65° C. and at an absolute pressure of between 190 mbar and 210 mbar. Still more preferably, the blood-derived product is albumin and the viral inactivation phase is carried out at a temperature of between 59.5° C. and 60.5° C. at an absolute pressure of 200 mbar. When the blood-derived product is albumin, the viral inactivation phase preferably lasts between 10 and 11 hours.

Alternatively, the blood-derived product is FACTOR VIII and the viral inactivation phase is carried out at a temperature of between 80° C. and 82° C. at an absolute pressure of between 450 and 550 mbar.

These pressure and temperature conditions in the viral inactivation phase are such that the steam is in the gaseous phase.

Preferably, the containers are bags made of a plastics material. Alternatively, the containers are vials. In an alternative form, the containers are made of another material that allows the blood-derived product to be contained while meeting the health standards in this respect.

BRIEF DESCRIPTION OF THE DRAWING

FIG. 1 is a diagram showing the phases of the method according to the present invention.

DETAILED DESCRIPTION

For a better understanding, the accompanying diagram of an embodiment of the present invention is provided as an explanatory but non-limiting example.

FIG. 1 shows a filling phase -1- of the container for a blood-derived product, a second viral inactivation phase -2-, with an access inlet -2'- for steam at sub-atmospheric pressure, and a third quality control phase -3- with subsequent storage -4-.

In a first embodiment by way of example, the method of preparing containers for blood-derived product uses albumin as said product. In the filling phase -1-, the container is filled. In this embodiment, the containers are preferably bags made of a plastics material. In the viral inactivation phase -2-, the viral inactivation is carried out using steam in direct contact with the bags made of a plastics material at sub-atmospheric pressure. Said phase is carried out at a temperature of between 55° C. and 65° C. and at an absolute pressure of between 190 mbar and 210 mbar. In a more preferred embodiment, said phase is carried out at between 59.5° C. and 60.5° C. and at an absolute pressure of 200 mbar.

During said viral inactivation phase -2-, the bags are subjected to the above-mentioned temperature and pressure conditions for a prolonged period of between 10 and 11 hours. A prolonged time under these temperature and pressure conditions implies a stress test and a sealing test for the bags in which small, existing defects are magnified. If the bags have any defect, the steam used would be capable of penetrating said bags, said penetration being visible with the naked eye, making the visual detection of defects easier.

Next, a process of cooling the bags made of a plastics material takes place. Said cooling process is an air-cooling process. In addition, it is advisable to incorporate an air venting system. Preferably, the air is filtered through a sterilizing filter.

Finally, the quality control phase -3- comprises a visual inspection. In this phase, among other things, sealing defects are inspected, said defects being, for example, defective welding in the container, breaks in the container, splits and porosities in the walls of the container, as well as other types of defects.

The object of the quality control is to discard defective containers. To do this, means for artificial viewing and image processing, for example, may be used. According to the present invention, defects may be detected by detecting water in the containers.

Alternatively, in this first embodiment, glass containers may be used.

In a second embodiment by way of example, the method of preparing containers for blood-derived products uses FACTOR VIII as said product. In the filling phase -1-, the container is filled. In this embodiment, the containers are usually vials. Alternatively, said containers may be of any other type. After filling, the product is lyophilised and after said lyophilisation a viral inactivation phase -2- is carried out. In the viral inactivation phase -2-, the viral inactivation is carried out by means of steam in direct contact with the bags made of a plastics material at sub-atmospheric pressure. Said phase is carried out at a temperature of between 80° C. and 82° C. and at an absolute pressure of between 450 and 550 mbar.

During said viral inactivation phase -2-, the bags are subjected to the above-mentioned temperature and pressure conditions for a prolonged period of between 72 and 74 hours. A prolonged time under these temperature and pressure conditions implies a stress test and a sealing test for the bags in which small, existing defects are magnified. If the bags have any defect, the steam used would be capable of penetrating said bags, said penetration being visible with the naked eye, making the visual detection of defects easier.

Next, a process of cooling the vials takes place. Said cooling process is an air-cooling process. In addition, it is advisable to incorporate an air venting system. Preferably, the air is filtered through a sterilizing filter.

Finally, the quality control phase -3- comprises a visual inspection. In this phase, among other things, sealing defects are inspected, said defects being, for example, defective welding in the container, breaks in the container, splits and porosities in the walls of the container, as well as other types of defects.

The object of the quality control is to discard defective containers. To do this, means for artificial viewing and image processing, for example, may be used. According to the present invention, defects may be detected by detecting water in the containers.

Various tests have been carried out using bags with no defects and control bags with defects and it was demonstrated that for the bags with defects, steam penetrated therein, and for the bags with no defects the steam did not penetrate, which demonstrates the viability of the method described in this application, both for the viral inactivation phase and for the detection of defects.

Although the invention has been described and illustrated on the basis of various representative examples, it should be understood that said embodiments given by way of example in no way limit the present invention, and therefore any of the variations included directly or as an equivalent in the content of the accompanying claims should be considered as included within the scope of the present invention.

What is claimed is:

1. A method of preparing containers for blood-derived products which comprises:
   filling the blood-derived product containers with a blood-derived product,
   inactivating viruses in the blood-derived product containers,
   detecting possible defects in the blood-derived product containers,
   wherein inactivating the viruses is carried out by placing the blood-derived product containers in contact with steam at a sub-atmospheric pressure in a chamber adapted for that purpose.

2. The method according to claim 1, further comprising cooling the blood-derived product containers after inactivating the viruses.

3. The method according to claim 2, wherein the cooling is carried out by placing the containers for blood-derived products in contact with purified water.

4. The method according to claim 1, wherein the steam used in inactivating the viruses is sanitary quality steam.

5. The method according to claim 1, wherein the steam used in inactivating the viruses is saturated steam.

6. The method according to claim 1, wherein detecting the possible defects comprises a visual inspection of the containers in order to locate defects in said containers.

7. The method according to claim 1, wherein the blood-derived product is therapeutic albumin and inactivating the viral viruses is carried out at a temperature of between 55° C. and 65° C. at an absolute pressure of between 190 mbar and 210 mbar.

8. The method according to claim 1, wherein the blood-derived product is therapeutic albumin and inactivating the viruses is carried out at a temperature of between 59.5° C. and 60.5° C. and at an absolute pressure of 200 mbar.

9. The method according to claim 1, wherein inactivating the viruses lasts between 10 and 11 hours.

10. The method according to claim 1, wherein the blood-derived product is FACTOR VIII and inactivating the viruses is carried out at a temperature of between 80° C. and 82° C. at an absolute pressure of between 450 and 550 mbar.

11. The method according to claim 10, wherein inactivating the viruses lasts for between 72 and 74 hours.

12. The method according to claim 1, wherein the containers are bags made of a plastic material.

13. The method according to claim 1, wherein the containers are vials.

* * * * *